(12) United States Patent
Heydlauf (10) Patent No.: US 11,005,938 B2
(45) Date of Patent: May 11, 2021

(54) DATA ROUTER-MEDIATED PUBLISHER/SUBSCRIBER TRANSMISSION ARCHITECTURE APPARATUS AND METHODS

(71) Applicant: Siemens Healthcare Diagnostics Inc., Tarrytown, NY (US)

(72) Inventor: Michael Heydlauf, Cary, NC (US)

(73) Assignee: Siemens Healthcare Diagnostics Inc., Tarrytown, NY (US)

( * ) Notice: Subject to any disclaimer, the term of this patent is extended or adjusted under 35 U.S.C. 154(b) by 0 days.

(21) Appl. No.: 15/733,347

(22) PCT Filed: Jan. 25, 2019

(86) PCT No.: PCT/US2019/015123
§ 371 (c)(1),
(2) Date: Jul. 6, 2020

(87) PCT Pub. No.: WO2019/160668
PCT Pub. Date: Aug. 22, 2019

(65) Prior Publication Data
US 2020/0396291 A1      Dec. 17, 2020

Related U.S. Application Data

(60) Provisional application No. 62/630,914, filed on Feb. 15, 2018.

(51) Int. Cl.
*H04L 29/08* (2006.01)
*G16H 10/40* (2018.01)
(Continued)

(52) U.S. Cl.
CPC ............. *H04L 67/12* (2013.01); *G16H 10/40* (2018.01); *G16H 10/60* (2018.01); *G16Y 10/60* (2020.01); *G16Y 20/10* (2020.01); *H04L 45/70* (2013.01)

(58) Field of Classification Search
CPC combination set(s) only.
See application file for complete search history.

(56) References Cited

U.S. PATENT DOCUMENTS 7,953,613 B2   5/2011   Gizewski
8,364,500 B2   1/2013   Eisenberger et al.
(Continued)

OTHER PUBLICATIONS

International Search Report for PCT/US2019/015123 dated Apr. 15 2019.
(Continued)

*Primary Examiner* — Xavier S Wong (57) ABSTRACT

Methods and apparatus for publisher-independent auxiliary communications in data router-mediated publisher/subscriber transmission architectures provide faster processing of actionable information by subscribers and increased flexibility to add publishers to a system. Publisher-originated information in a publisher-specific format is used by either the publisher, or a data router coupled to the publisher, to generate information, based on the publisher-originated information, in a publisher-independent format recognized by subscribers, and provided by the data router to subscribers. Publishers may include analyzers such as blood, immuno-assay, and clinical chemistry analyzers, IoT devices, and automation systems.

20 Claims, 8 Drawing Sheets

(51) Int. Cl.
  *G16H 10/60* (2018.01)
  *G16Y 20/10* (2020.01)
  *G16Y 10/60* (2020.01)
  *H04L 12/721* (2013.01)

(56) References Cited

U.S. PATENT DOCUMENTS

| | | |
|---|---|---|
| 10,142,201 B2 * | 11/2018 | Verma .................... H04L 67/28 |
| 2008/0004904 A1 | 1/2008 | Tran |
| 2008/0040151 A1 | 2/2008 | Moore |
| 2008/0240160 A1 | 10/2008 | Ishii |
| 2011/0307568 A1 | 12/2011 | Reed et al. |
| 2012/0289787 A1 | 11/2012 | Kurgan et al. |
| 2014/0143855 A1 * | 5/2014 | Keoh ................... H04L 63/123 726/14 |
| 2014/0244710 A1 * | 8/2014 | Sharma ................. H04W 4/21 709/201 |
| 2015/0019553 A1 | 1/2015 | Shaashua et al. |
| 2020/0169295 A1 * | 5/2020 | Pierson ............... H04B 5/0031 |

OTHER PUBLICATIONS

Ziminski, "A Study of Architectural Alternatives for Integrating Health Care Data and Systems"; Jun. 29, 2009.

\* cited by examiner

DATA ROUTER-MEDIATED PUBLISHER/SUBSCRIBER TRANSMISSION ARCHITECTURE APPARATUS AND METHODS

FIELD

This application relates generally to methods and apparatus for publisher-independent auxiliary communications in a data router-mediated publisher/subscriber transmission architecture. This application further relates to a data router-mediated publisher/subscriber transmission architecture for healthcare laboratory automation.

BACKGROUND

Automated diagnostic analysis apparatus (e.g., chemical analyzers or immunoassay instruments) may be used to analyze patient specimens. Patient specimens may include, e.g., urine, blood serum or plasma, saliva, cerebrospinal liquids, various tissue samples, and the like. Automated diagnostic analysis apparatus are used to improve operating speed and efficiency as compared to (1) manual operation of analyzers or instruments; (2) manual transport and positioning of specimen containers; and (3) manual recordation and transmission of test, measurement, and analysis information.

Automated diagnostic analysis apparatus in a laboratory setting are frequently configured to operate with multiple pieces of equipment and a track system for the transport of samples or specimens. A process manager may be incorporated in such a system to direct the operation of the various analyzers, transport tracks, centrifuges, environmental sensors, and the like. Such process managers receive information about the various apparatus and operations, and generate control information based thereon.

SUMMARY

According to a first embodiment, a method, includes obtaining, by a first device, a first measured result; generating, by the first device, a first data packet in a first format, the first data packet based, at least in part, on the first measured result, and the first format associated with the first device; generating, by the first device, a second data packet in a second format, the second data packet based, at least in part, on a portion of the first data packet, and the second format being independent of the first device; and transmitting the first data packet in the first format and the second data packet in the second format via a first communications network; wherein the second data packet in the second format contains actionable information derived from the first data packet in the first format, and wherein the first device comprises an analyzer, an automation system, or an IoT device. The analyzer may be, but is not limited to, a blood analyzer, an immunoassay analyzer, or a clinical chemistry analyzer.

According to another embodiment, a method, includes obtaining, by a device, a first measured result; generating, by the device, a first data packet in a first format, the first data packet based, at least in part, on the first measured result, and the first format associated with the device; transmitting, by the device, the first data packet in the first format to a data router via a first communications network; generating, by the data router, a second data packet in a second format, the second data packet based, at least in part, on a portion of the first data packet, and the second format being independent of the device; and transmitting, by the data router, the first data packet in the first format and the second data packet in the second format to a subscriber via a second communications network; wherein the second data packet in the second format contains actionable information derived from the first data packet in the first format. The device may be an analyzer, an automation system, or an IoT device. The analyzer may be, but is not limited to, a blood analyzer, an immunoassay analyzer, or a clinical chemistry analyzer.

According to another embodiment, a health information system, includes a first device configured to obtain a measured parameter, and further configured to generate a first data packet in a first format, the first data packet based, at least in part, on the measured parameter, and the first format associated with the first device; a subscriber; a data router coupled to the first device via a first network and coupled to the subscriber via a second network, the data router including a processor; a memory, coupled to the processor, the memory having stored therein a plurality of instructions that, when executed by the processor, causes the data router to: receive the first data packet in the first format via the first network, generate a second data packet in a second format, the second data packet based, at least in part, on a portion of the first data packet, and the second format being independent of the first device, and transmit the first data packet and the second data packet to the subscriber via the second network; wherein the second data packet in the second format contains actionable information derived from the first data packet in the first format.

According to another embodiment, an apparatus, includes a processor; and a memory coupled to the processor, the memory having instructions stored therein that, when executed by the processor, cause the apparatus to: obtain a first measured result, generate a first data packet in a first format, the first data packet based, at least in part, on the first measured result, and the first format associated with the apparatus, generate a second data packet in a second format, the second data packet based, at least in part, on a portion of the first data packet, and the second format being independent of the apparatus, and transmit the first data packet and the second data packet via a communications network; wherein the second data packet in the second format contains actionable information derived from the first data packet in the first format.

Still other aspects, features, and advantages of this disclosure may be readily apparent from the following detailed description illustrated by a number of example embodiments and implementations, including the best mode contemplated. This disclosure may also be capable of other and different embodiments, and its several details may be modified in various respects. Accordingly, the drawings and descriptions are to be regarded as illustrative in nature, and not as restrictive. The drawings are not necessarily drawn to scale. This disclosure covers all modifications, equivalents, and alternatives falling within the scope of the subjoined claims.

DETAILED DESCRIPTION

Overview

Digitalization, Artificial Intelligence (AI) and the Internet of Things (IoT) are emerging technologies that are rapidly affecting a number of industries, including healthcare. These emerging technologies deal with, among other things, the acquisition and analysis of data. Systems that facilitate data gathering, and offer augmentation of that data for seamless action and insights are believed to be of particular value in the marketplace in general, and in healthcare laboratory automation systems in particular.

Various embodiments, in accordance with this disclosure, provide a data router coupled between one or more publishers, and one or more subscribers.

In some example embodiments, the data router is a combination of hardware and software that acts as a broker between data sources (i.e., publishers) and data consumers (i.e., subscribers). In various alternative embodiments, the data router may be implemented as hardware, e.g., logic circuits, without software intended to be executed by a processor. Publishers register a "channel" with the data router.

In various embodiments, the channel is a logical construct that allows a publisher to label information that conforms to certain constraints and conditions such that the labelled information can be recognized by the data router as originating from a specific publisher's registered channel. In some example embodiments, registering a channel by the publisher with the data router includes communication between the publisher and the data router, together with action by both the publisher and the data router. The communication between the publisher and the data router may be conducted through any suitable means, wired or wireless. The action taken by the publisher is to maintain a channel identification label that accompanies its published information packets so that the data router can properly store the data and later provide the data associated with that channel to a subscriber that requests data from that channel.

After registering a channel with the data router, a publisher may send data in any predetermined format, to the data router. In some example embodiments, the data router is format/protocol agnostic, meaning that the data router may accept the data sent by the publisher in any predetermined format. In some example embodiments data is sent from the publisher to the data router via a communications network, such as but not limited to a local area network (LAN). In other example embodiments data is sent from the publisher to the data router via the Internet. The publishers and the data router may be physically co-located, or may be physically remote from each other. The communications network between the publisher and the data router may be wired, wireless, or a combination of wired and wireless.

Subscribers are consumers of the information generated by the publishers. In example embodiments that have a plurality of publishers, a subscriber may be interested in receiving information from one or more specific combinations of publishers. The subscribers register, with the data router, those channels in which they are interested. That is, a subscriber communicates with the data router to identify the channels from which it wants to receive published data or information. The subscriber then receives the requested published data or information from the corresponding publisher(s) as it becomes available. In some example embodiments, the data router can store published data until all of the subscribers to a channel have received it.

In various example embodiments, the subscribers use the data or information received from the publishers, in a publisher-independent format, via the data router and corresponding communications networks, to initiate control actions. In some embodiments, the publisher-independent format data or information is used to initiate control actions prior to the publisher-specific format data or information being used. In example embodiments, a subscriber may receive data or information in both a publisher-specific, and a publisher-independent format; and the subscriber processes the data or information in the publisher-independent format first. As explained in detail below, the second format (publisher-independent format) provides, among other things, faster processing of actionable information. For example, the received data or information in the publisher-independent format may indicate to the subscriber that an alert condition exists. An alert condition is one in which action is to be initiated and may include, but is not limited to, directing that physical action is needed by an automation system, analyzer, instrument, centrifuge, sensor, and the like in, for example, a medical laboratory setting.

Terminology

As used herein, the term "publisher" refers to a device that is configured to, among other things, provide data to a data router. Publishers may be, but are not limited to, laboratory diagnostic analyzers, automation systems, informatics products, and IoT devices.

As used herein, "data router" refers to a computational resource, e.g., a computer system, that is configured to receive data from one or more publishers, and organize the received data for transmission in one or more channels. Such data routers are further configured to store, at least temporarily, some or all of the received data.

As used herein, "subscriber" refers to a computational resource that is configured to present a request, to a data router, for information from one or more publishers, or more specifically from one or more channels. A subscriber may be further configured to receive the requested information from the one or more channels via the data router which transmits data associated with the requested one or more channels to the subscriber. A subscriber can be any system or subsystem that uses data, and may be, but is not limited to, an informatics product, a third party application (e.g., software executed by a computational resource), etc.

As used herein, "computational resource" refers to a device configured to carry out one or more predetermined data processing and/or data communication tasks. Such computational resources can be implemented entirely by hardware, e.g., digital circuits, or by a combination of a processor and a memory having instructions stored therein that, when executed by the processor, cause the computational resource to perform the one or more predetermined data processing and/or data communication tasks.

The term "IoT" is an acronym for Internet of Things.

As used herein, "IoT device" refers to a device that is configured to make one or more measurements of its environmental or ambient conditions, generate data based on the one or more measurements, and transmit that data by wired or wireless communication, or a combination of wired and wireless communication. IoT devices may be, but are not limited to, temperature sensors, pressure sensors, barometers, humidity sensors, and water ionization sensors.

Figure 1:
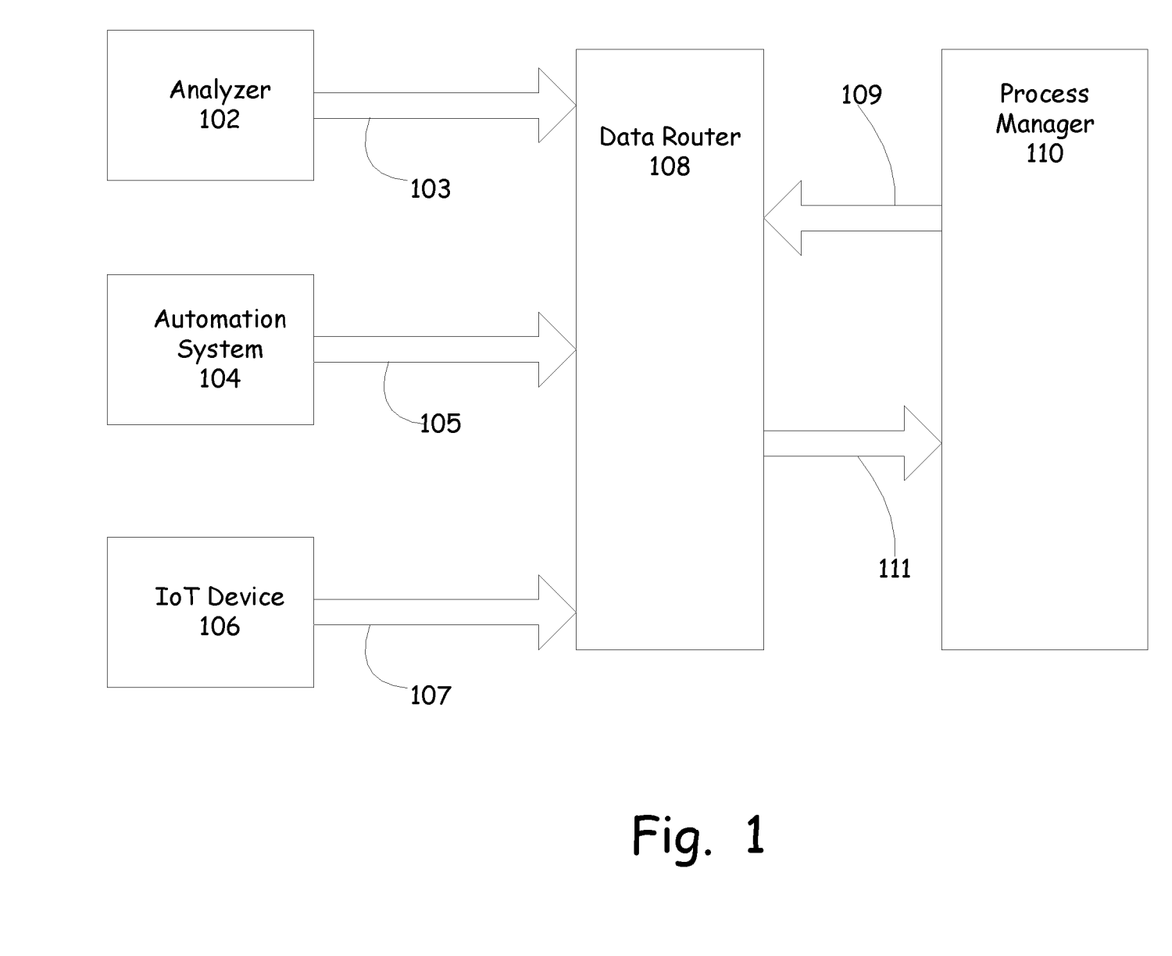
FIG. 1 illustrates a block diagram of publishers and a subscriber coupled by a data router and showing data flow in accordance with various example embodiments.

FIG. 1 illustrates an example laboratory network, in accordance with some embodiments of this disclosure, having publishers 102, 104, and 106. In this example embodiment, publisher 102 is an analyzer such as, but not limited to, a blood analyzer, immune-assay analyzer, and clinical chemistry analyzer. Publisher 104, in the example embodiment, is an automation system that provides a track system for moving samples between analyzers. In addition to the track itself, there may be other automation-specific modules present on the track such as one or more centrifuges, one or more refrigerated storage units, one or more bulk input modules, one or more decappers, and the like. Publisher 106, in the example embodiment, is an IoT device, such as but not limited to one or more temperature sensors, pressure sensors, barometers, humidity sensors, and water ionization sensors. Publishers 102, 104, and 106, communicate information 103, 105, 107 they respectively obtain in the course of their operations. Information 103, 105, and 107 may be in a publisher-specific format. That is, each publisher 102, 104, and 106 may present information in its own specific format.

FIG. 1 further shows that information 103, 105, and 107 are communicated to a data router 108. In this example embodiment, data router 108 may be a computer system, and information 103, 105, 107 may be communicated between publishers 102, 104, 106 respectively and data router 108 via any suitable communications network, wired or wireless.

Still referring to FIG. 1, a subscriber 110 is shown wherein subscriber 110 is a process manager, for example. The processor manager may be implemented as a computer system executing one or more programs. As described above, a subscriber may make a request 109 to receive data or information, originally generated by a publisher, via a requested channel 111 from data router 108. In such an arrangement, the subscriber 110 to the data router 108 interrogates the packets or messages transmitted by the data router 108, and decides how to interpret that data or information. One such common interpretation is whether or not the data or information represents an alert, that is, something a user should know about or is otherwise actionable. Unfortunately in conventional systems, the contents of the packets or messages transmitted by a data router have formats that may be specific to the hardware and/or software of the publishers communicating with the data router. This creates a dependency whereby every new data publisher added to a system requires a new version of the subscriber to properly interpret the new publisher's data.

Various embodiments in accordance with this disclosure overcome the subscriber's dependency on publisher-specific formatting of packets or messages.

Some embodiments in accordance with this disclosure provide a publisher that can identify alertable data in a generic way. This identification can be performed by the publisher itself, or by a custom driver created as a companion to the data publisher. Subscribers can identify alertable data from the data router and act upon it in a common way. For example, as part of the data payload sent from the data router to a subscriber, a message header can contain all of the information a subscriber would need to process an alert. An example publisher-independent format for alertable data is shown in Table 1 below.

TABLE 1

| Name of Field | Content of Field |
| --- | --- |
| Date/Time of Occurrence | date/time stamp of when an alert occurred |
| Alert ID | a unique ID of a specific alert from a publisher |
| Device ID | an identifier of the device or system with which the alert is associated. This may be used by subscribers to map a device from an external system to an internal device representation. |
| Alert Category | a category identifier that may be used to group similar alerts from a publisher together, or to display a common alert icon for a given category |
| Alert Severity | one of a number of pre-established severities, e.g., informational, warning, or critical |
| Alert Status | the status of the alert, e.g., new, update or resolved. This field may enable an alert publisher to signal to its subscribers that a previously communicated alert condition has been resolved, thereby enabling subscribers to take appropriate action (e.g., remove a displayed alert condition). |
| Alert Description | freeform text describing the nature of the alert |

In various embodiments in accordance with this disclosure, a subscriber, aware of the publisher-independent messaging convention, may identify and act upon a packet or message from any publisher that contains an alert header in the publisher-independent format. In this way, new publishers can participate in an existing subscriber's application workflow without any specific changes or updates needed in the subscriber. This technological solution provides subscribers with an improved ability to respond to alerts, and further provides the ability to integrate additional publishers to a system without having to make changes to the subscriber.

Figure 2:
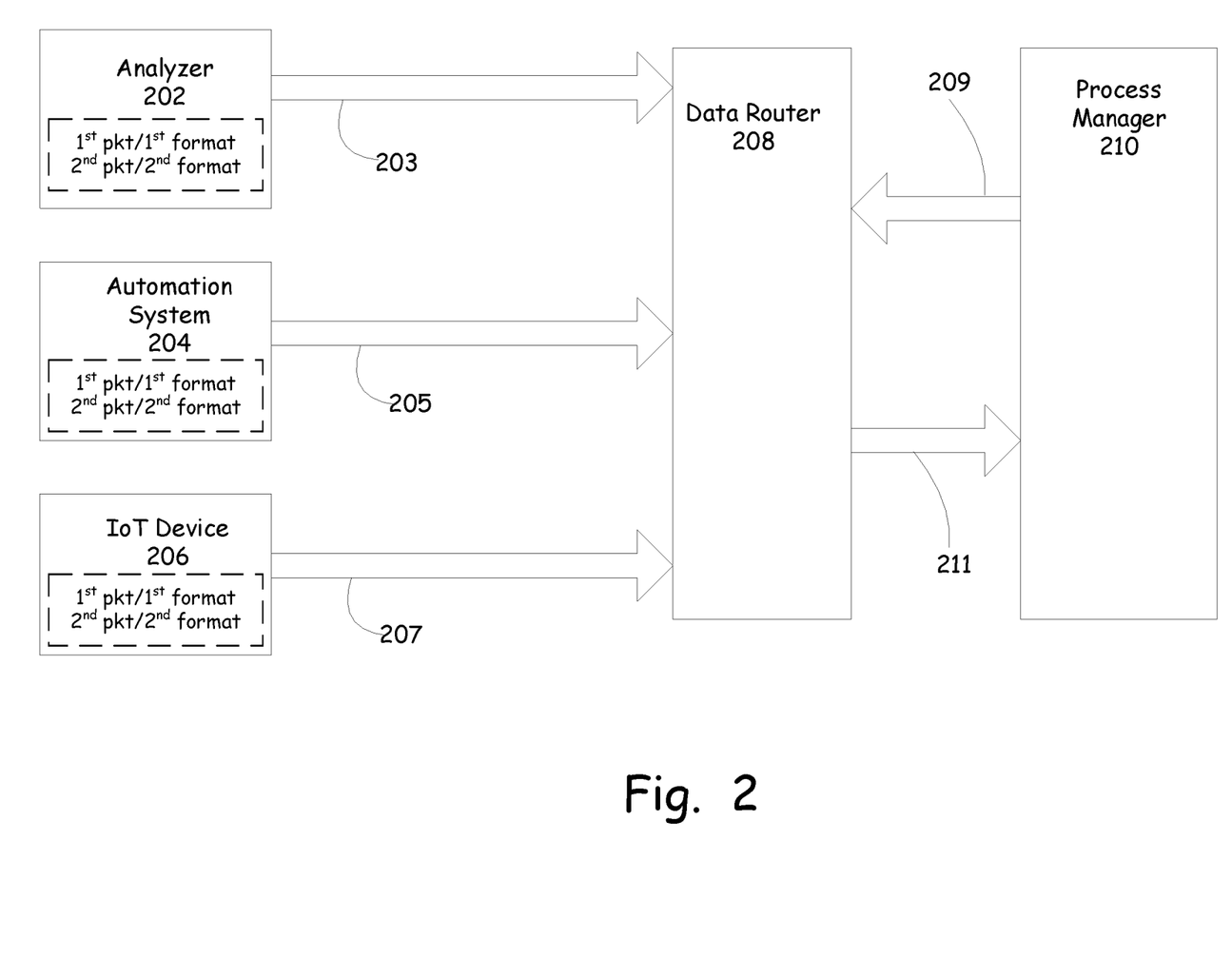
FIG. 2 illustrates a block diagram of publishers and a subscriber coupled by a data router and showing data flow, wherein the publishers are configured to provide actionable information in a publisher-independent format in accordance with various example embodiments.

FIG. 2 illustrates an example laboratory network, in accordance with some embodiments of this disclosure, having publishers 202, 204, and 206. In this example embodiment, publishers 202, 204, and 206 are each configured to measure various parameters, generate, and/or obtain data or information and produce, via hardware or hardware/software combinations, first packets of data or information in a native format, i.e., a publisher-specific format, and are each further configured to produce second packets of data or information based, at least in part, on the respective first packets, with the second packets of data or information being in a publisher-independent format, e.g., the format described in Table 1, above. The aforementioned hardware/software combinations refer to computer systems such as the computer system discussed below in connection with FIG. 6.

Such computer systems accomplish their tasks by executing instructions stored in their respective memories. By executing such instructions the first packets of data or information and the second packets of data or information are logically constructed, formatted, and/or communicated. In this example embodiment, publisher 202 is an analyzer such as, but not limited to, a blood analyzer. Publisher 204 is an automation system that provides a track system for moving samples between analyzers. As an automation system, publisher 204 may obtain data related to a status of the automation system functions to produce a first automation system report for eventual communication to a subscriber. Publisher 206 is an IoT device, such as but not limited to one or more temperature sensors, pressure sensors, barometers, humidity sensors, and water ionization sensors. As an IoT device, publisher 206 may obtain data related to a sensor of the IoT device to produce a first IoT report. Publishers 202, 204, and 206, communicate information 203, 205, 207 they respectively obtain in the course of their operations. In this example embodiment, information 203, 205, and 207 includes data or information in a publisher-specific format, and further includes information based on at least a portion of the obtained information and generated in a publisher-independent format, different from the publisher-specific format. That is, in this example embodiment, each publisher presents information in its own specific format, and also generates and presents at least a portion of that information in a publisher-independent format.

FIG. 2 further shows that information 203, 205, and 207 are communicated to a data router 208. In this example embodiment, data router 208 may be a computer system, and information 203, 205, 207 may be communicated between publishers 202, 204, 206 respectively and data router 208 via any suitable communications network, wired or wireless.

Still referring to FIG. 2, a subscriber 210 is shown wherein subscriber 210 is a process manager. The subscriber 210 may be implemented as a computer system executing one or more programs. As described above, a subscriber may make a request 209 to receive data or information, originally generated by a publisher, via a requested channel 211 from data router 208. In such an arrangement, subscriber 210 receives data or information in both the publisher-specific format and in the publisher-independent format. An example publisher-independent format for alertable data is shown in Table 1 above. This technological solution provides subscribers with an improved ability to respond to alerts, and further provides the ability to integrate additional publishers to a system without having to make changes to the subscriber.

Figure 3:
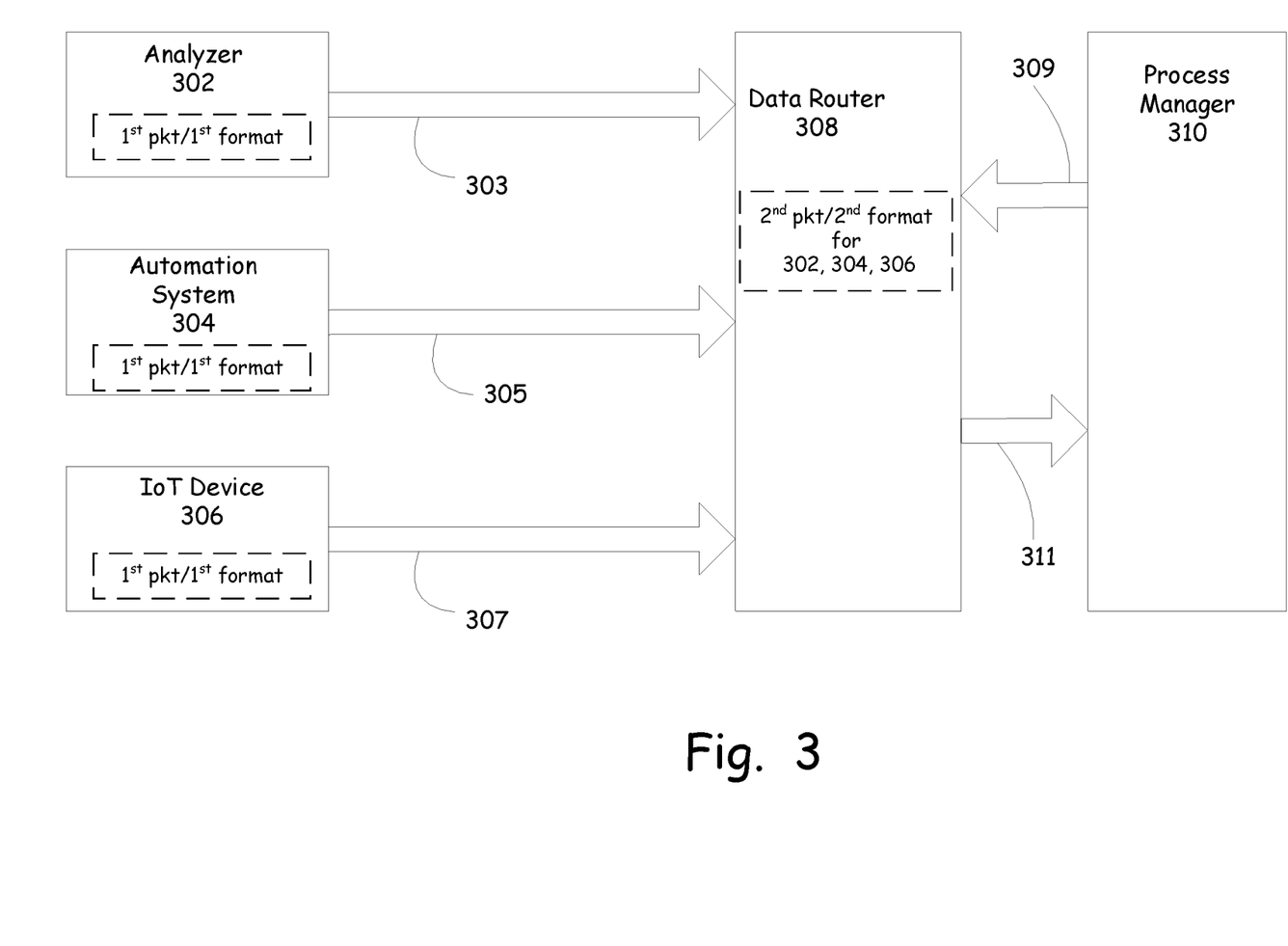
FIG. 3 illustrates a block diagram of publishers and a subscriber coupled by a data router and showing data flow, wherein the data router is configured to generate actionable information in a publisher-independent format in accordance with various example embodiments.

FIG. 3 illustrates an example laboratory network, in accordance with some embodiments of this disclosure, having publishers 302, 304, and 306. In this example embodiment, publishers 302, 304, and 306 are each configured to measure various parameters, generate, and/or obtain data or information and produce, via hardware or hardware/software combinations, first packets of data or information in a native format, i.e., a publisher-specific format, which are then communicated to a data router via a communications network. The data router is configured to produce second packets of data or information based, at least in part, on the respective first packets, with the second packets of data or information being in a publisher-independent format, e.g., the format described in Table 1, above. In this example embodiment, publisher 302 is an analyzer such as, but not limited to, a blood analyzer. Publisher 304 is an automation system that provides a track system for moving samples between analyzers. Publisher 306 is an IoT device, such as, but not limited to one or more temperature sensors, pressure sensors, barometers, humidity sensors, and water ionization sensors. Publishers 302, 304, and 306, communicate information 303, 305, 307 they respectively obtain in the course of their operations. In this example embodiment, information 303, 305, and 307 includes data or information in a publisher-specific format.

FIG. 3 further shows that information 303, 305, and 307 are communicated to a data router 308. In this example embodiment, data router 308 may be a computer system, and information 303, 305, 307 may be communicated between publishers 302, 304, 306 respectively and data router 308 via any suitable communications network, wired or wireless. After receiving any one of information 303, 305, 307, data router 308 generates a corresponding second information packet in a publisher-independent format which is stored along with the information received from the published for an identified channel. The second information packet may be stored, for example, in a memory local to or remote from data router 308.

Still referring to FIG. 3, a subscriber 310 is shown wherein subscriber 310 is a process manager. The subscriber (processor manager) 310 may be implemented as a computer system executing one or more programs. As described above, a subscriber may make a request 309 to receive data or information, originally generated by a publisher, via a requested channel 311 from data router 308. In such an arrangement, subscriber 310 receives data or information in both the publisher-specific format and in the publisher-independent format, with the publisher-independent format data or information being generated by the data router 308 rather than by the publishers 302, 304 or 306. An example publisher-independent format for alertable data is shown in Table 1 above. This technological solution provides subscribers with an improved ability to respond to alerts, and further provides the ability to integrate additional publishers to a system without having to make changes to the subscriber. Because subscribers receive data or information from data router 308 in a publisher-independent format that is organized to provide actionable data or information to the subscribers in a predetermined format regardless of the source of the data or information, the subscribers' processing burden is reduced compared to first having to determine which publisher-specific format is being used, and then choosing specific software modules to execute in order to extract actionable data or information. By reducing the subscribers' processing burden in accordance with embodiments of this disclosure, the subscribers' ability to quickly respond to actionable data or information is improved. Furthermore, by providing actionable data or information from data router 308 to subscribers in a publisher-independent format, publishers can be added to a system regardless of their publisher-specific data or information formats because the subscribers will be able to respond to actionable data or information without requiring modification in order to interpret additional publisher-specific formats.

Figure 4:
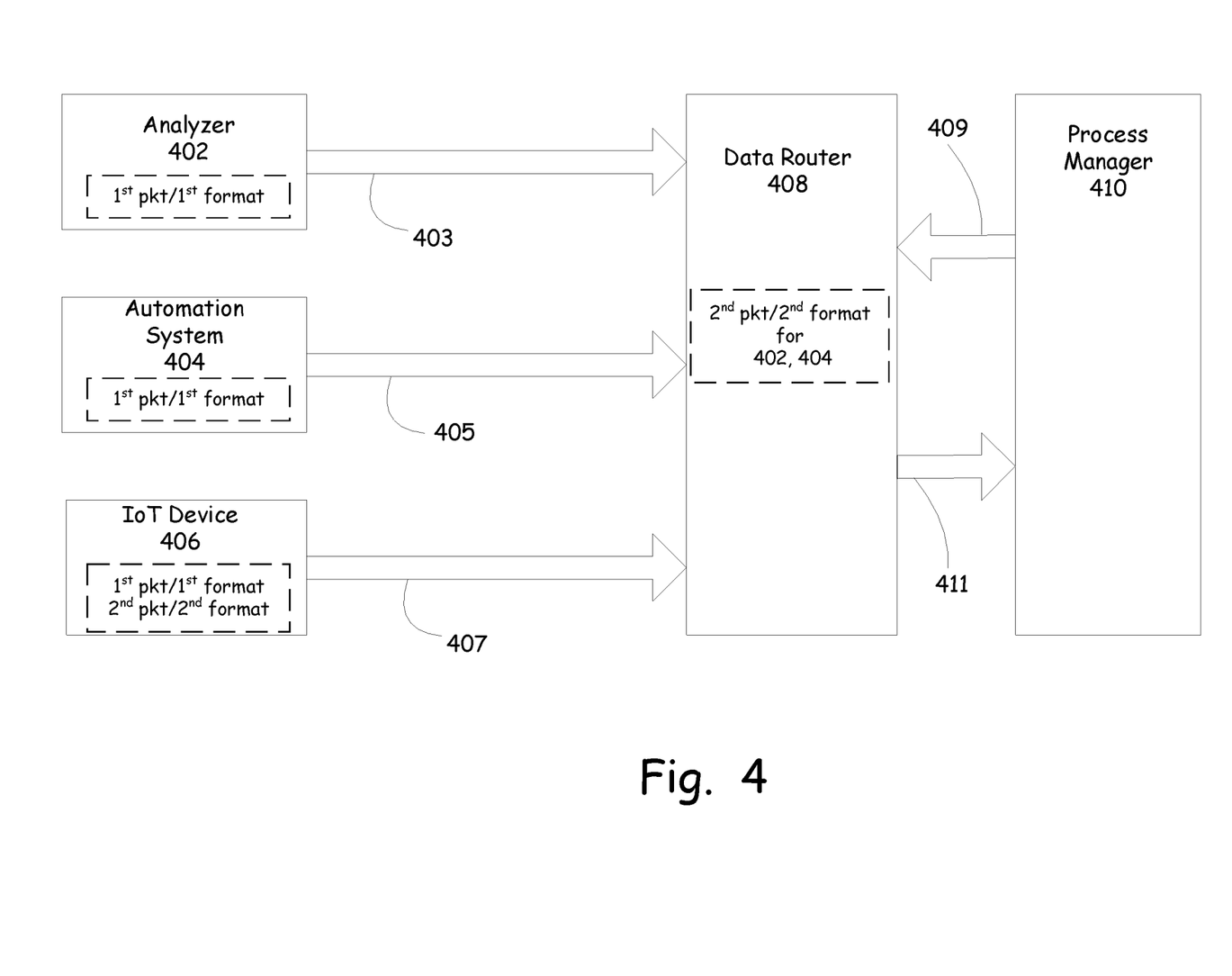
FIG. 4 illustrates a block diagram of publishers and a subscriber coupled by a data router and showing data flow, wherein a subset of the publishers are configured to provide actionable information in a publisher-independent format, and the data router is configured to generate actionable information in a publisher-independent format in accordance with various example embodiments.

FIG. 4 illustrates an example laboratory network, in accordance with some embodiments of this disclosure, having publishers 402, 404, and 406. In this example embodiment, publishers 402, and 404, are each configured to measure various parameters, generate, and/or obtain data or information and produce, via hardware or hardware/software combinations, first packets of data or information in a native format, i.e., a publisher-specific format, and then communicate those first packets to a data router. The data router is configured to produce second packets of data or information based, at least in part, on the respective first packets of publishers 402, 404, with the second packets of data or information being in a publisher-independent format, e.g., the format described in Table 1, above. In this example embodiment, publisher 402 is an analyzer such as, but not limited to, a blood analyzer. Publisher 404 is an automation system that provides a track system for moving samples between analyzers. Publisher 406 is an IoT device, such as but not limited to one or more temperature sensors, pressure sensors, barometers, humidity sensors, and water ionization sensors. Publishers 402, 404, and 406, communicate information 403, 405, 407 they respectively obtain in the course of their operations. In this example embodiment, information 403 and 405, includes data or information in a publisher-specific format, but information 407 includes data or information in both a publisher-specific format and in a publisher-independent format.

FIG. 4 further shows that information 403, 405, and 407 are communicated to a data router 408. In this example embodiment, data router 408 may be a computer system, and information 403, 405, 407 may be communicated between publishers 402, 404, 406 respectively and data router 408 via any suitable communications network, wired, wireless, or a combination of wired and wireless. After receiving any one of information 403 and 405, data router 408 generates a corresponding second information packet in a publisher-independent format which is stored along with the information received from the publishers 402 and 404 for an identified channel. However, in this example embodiment, data router 408 is configured to recognize that information 407 includes information in both the publisher-specific and publisher-independent formats. In this example embodiment, rather than simply storing and forwarding information 403, 405, and 407, data router 408 scans, i.e., analyzes, the incoming information 403, 405, and 407, to determine whether each publisher has transmitted data or information in both a publisher-specific and a publisher-independent format. In this example embodiment, the determination is made by data router 408 executing instructions stored in the memory of its computer system by which the information 403, 405, and 407 are compared to known, or otherwise predetermined (e.g., rule-based), formats. In the case where data router 408 determines that a publisher has only provided data or information in a publisher-specific format, data router 408 then generates a data packet in a publisher-independent format, e.g., the format shown in Table 1, above. In the case where data router 408 determines that a publisher has provided data or information in both a publisher-specific format, and a publisher-independent format, e.g., the format shown in Table 1 above, data router 408 does not generate data or information in a publisher-independent format. Thus data router 408 stores information 407, but does not generate an additional data packet in the publisher-independent format corresponding to information 407. Information 403, 405 and 407 may be stored in a memory, for example, local to or remote from data router 408.

Still referring to FIG. 4, a subscriber 410 is shown wherein subscriber 410 is a process manager. The subscriber (processor manager) 410 may be implemented as a computer system executing one or more programs, for example. As described above, a subscriber may make a request 409 to receive data or information, originally generated by a publisher, via a requested channel 411 from data router 408. In such an arrangement, subscriber 410 receives data or information in both the publisher-specific format and in the publisher-independent format. An example publisher-independent format for alertable data is shown in Table 1 above. This technological solution provides subscribers with an improved ability to respond to alerts, and further provides the ability to integrate additional publishers to a system without having to make changes to the subscriber.

In various embodiments in accordance with this disclosure, a healthcare information system does not require a new version of a process manager each time a publisher is added to the system because the logic to determine and declare a message as alertable is implemented by the publisher (or publisher driver) rather than being solely reliant on the subscriber. Alternatively, the logic to determine and declare a message as alertable may be implemented by the data router rather than being solely reliant on the subscriber. In further alternative embodiments, the logic to determine and declare a message as alertable is distributed such that a first group of publishers, from a plurality of publishers, is configured to perform this function, and a second group of publishers relies on the data router to perform this function.

The subscriber, in this example the process manager, may only need to interpret the publisher-independent data or information to process alerts In some embodiments, the subscriber can choose to ignore a publisher-independent message, and continue to provide custom message handling.

Figure 5:
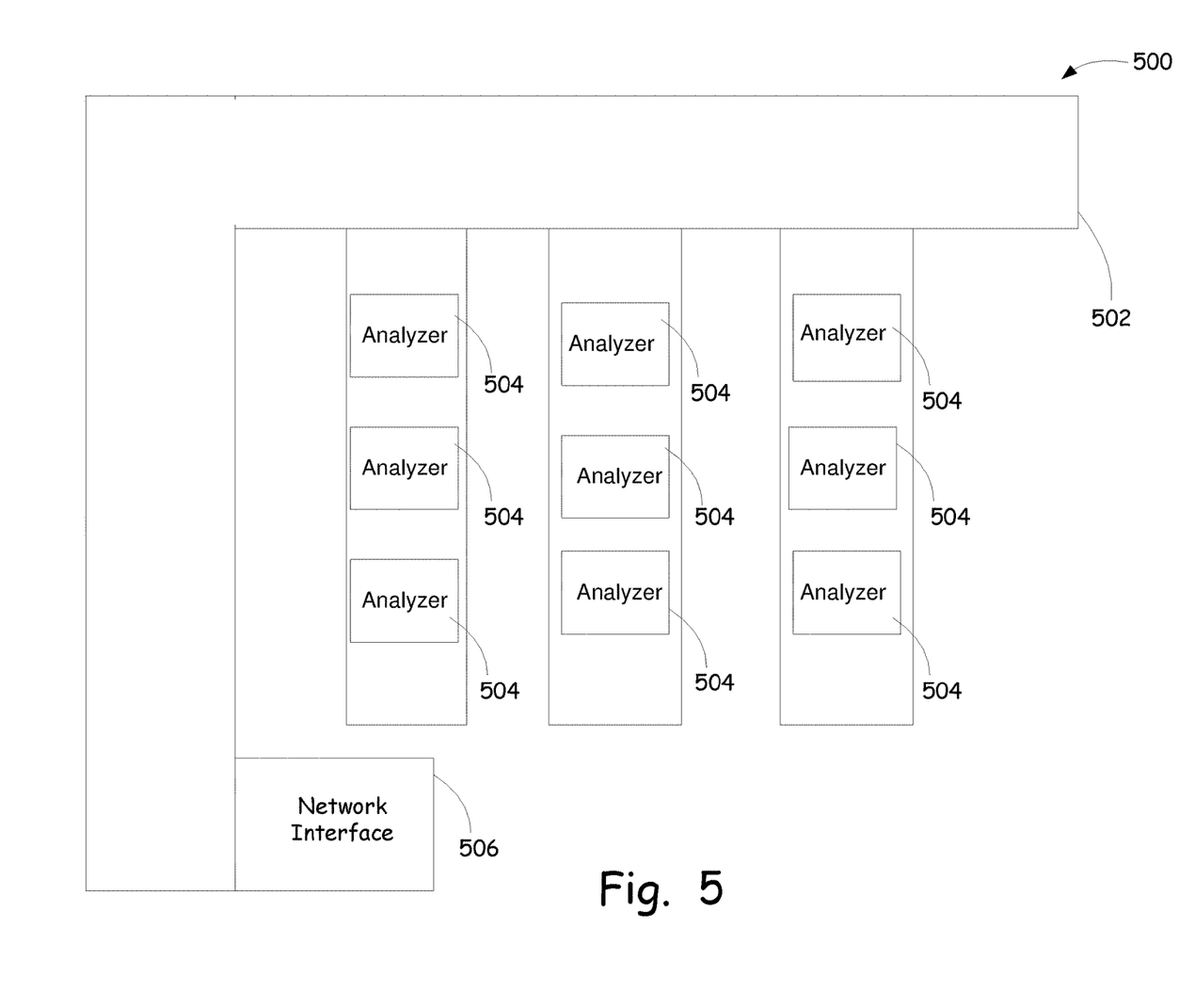
FIG. 5 illustrates an example automation system in accordance with various example embodiments.

FIG. 5 provides a high-level block diagram of an automation system 500 in accordance with various embodiments of this disclosure. The automation system 500 of FIG. 5, includes a track system 502 suitable for the transport of samples or specimens, in containers, to and from the various analyzers 504. It is noted that automation system 500 may also include other apparatus such as but not limited to centrifuges (not shown) disposed cooperatively with the track system 502 to deliver and pickup of sample or specimen containers. Such automation systems including track systems are well known in, for example, medical laboratory settings, for example, the Aptio® Laboratory Automation System, available from Siemens Healthcare Diagnostics, Inc. In operation, tracks convey sample or specimen containers between various lab stations such as, but not limited to, analyzers and centrifuges. Robots may be used to transfer sample or specimen containers from the track to a lab station, and from a lab station to the track. The aforementioned lab stations, may collect and/or generate data or information in the course of their respective operations, and communicate that data or information to automation system 500. Automation system 500 may also include a network interface 506 by means of which communications between the automation system 500 and a data router, such as data router 108, 208, 308 or 408, may be conducted. Automation system 500 may be configured to communicate the data or information from various lab stations, such as but not limited to, analyzers and centrifuges, to a data router via network interface 506. Network interface 506 may be any suitable hardware, or hardware/software combination, for conducting communications with a data router. Such communications may be wired, wireless, or a combination of wired and wireless, and may be point-to-point, or packet-switched such as in Internet-based communication.

Figure 6:
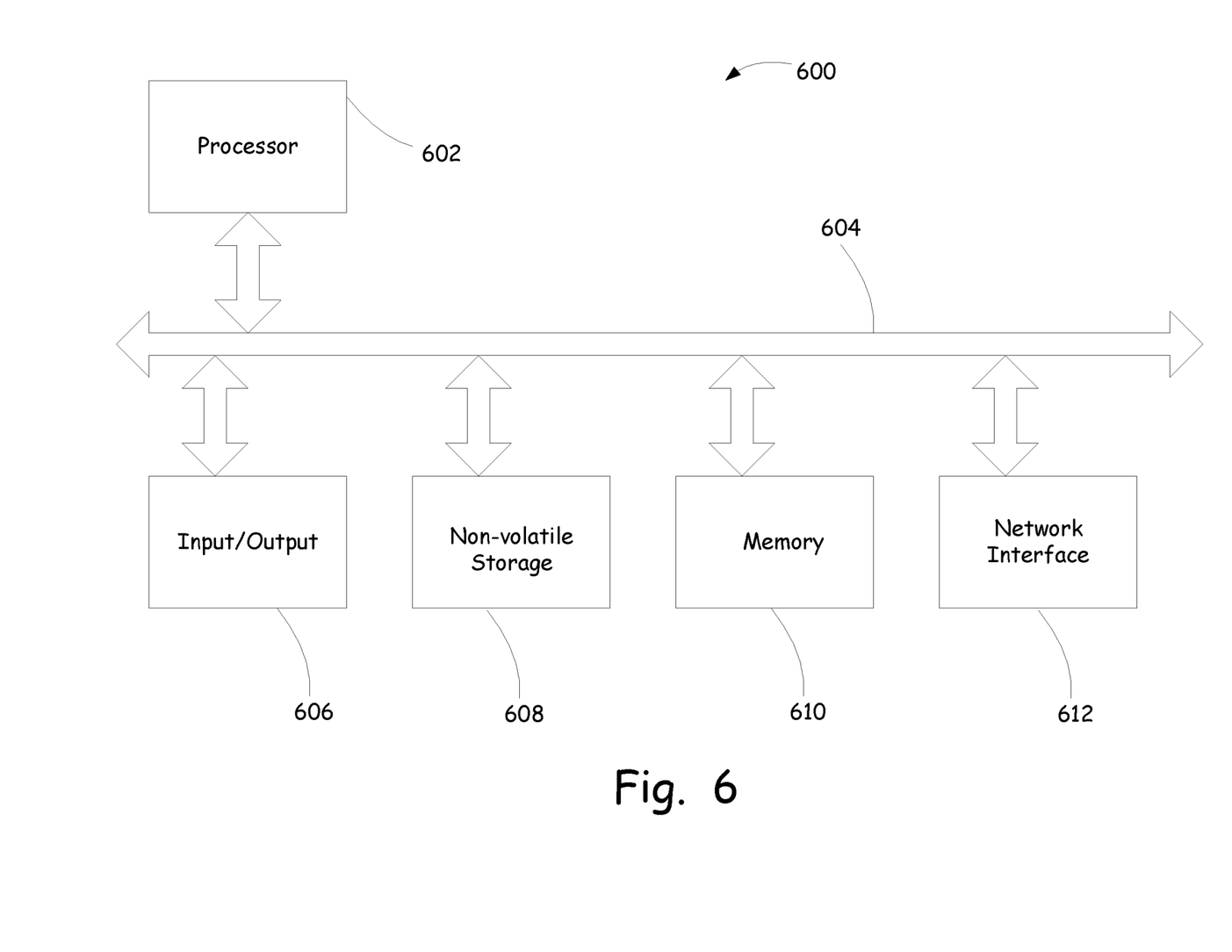
FIG. 6 illustrates an example computer system in accordance with various example embodiments.

FIG. 6 shows a high-level block diagram of an example computer system 600. In this example embodiment, a processor 602 may be coupled to other components of computer system 600 by a bus 604. An input/output device 606, such as but not limited to a display or a keyboard may be coupled to bus 604. A non-volatile storage 608, such as but not limited to a hard disk drive or a flash memory, may be coupled to bus 604. A memory 610, such as but not limited to a dynamic random access memory (DRAM), may be coupled to bus 604. Memory 610 may be configured to store therein instructions that may be executed by processor 602, and may be further configured to store data that does not represent instructions to be executed by processor 602. A network interface 612, such as but not limited to an Ethernet interface, may be coupled to bus 604. Network interface 612 provides a communications connection for computer system 600 to a communications network such as, but not limited to, a local area network, or via routers, to the Internet. In one or more embodiments, analyzer 102, 202, 302 or 402, and data router 108, 208, 308 or 408, may include a computer system similar to computer system 600. Analyzers, automation systems, and the like, and/or data routers that include a computer system similar to computer system 600, further include programs, i.e., instructions, stored in a memory and/or in a storage device such as but not limited to non-volatile storage 608 and memory 610. In operation, such analyzers, automation systems, and the like, and/or data routers that include a computer system similar to computer system 600, may execute instructions stored in their respective memories 610 by their respective processors 602 to implement functions such as, but not limited to, generating a first packet of data or information in a publisher-specific format or generating a second packet of data or information based, at least in part, on the content of the first packet of data or information in a processor-independent format.

Figure 7:
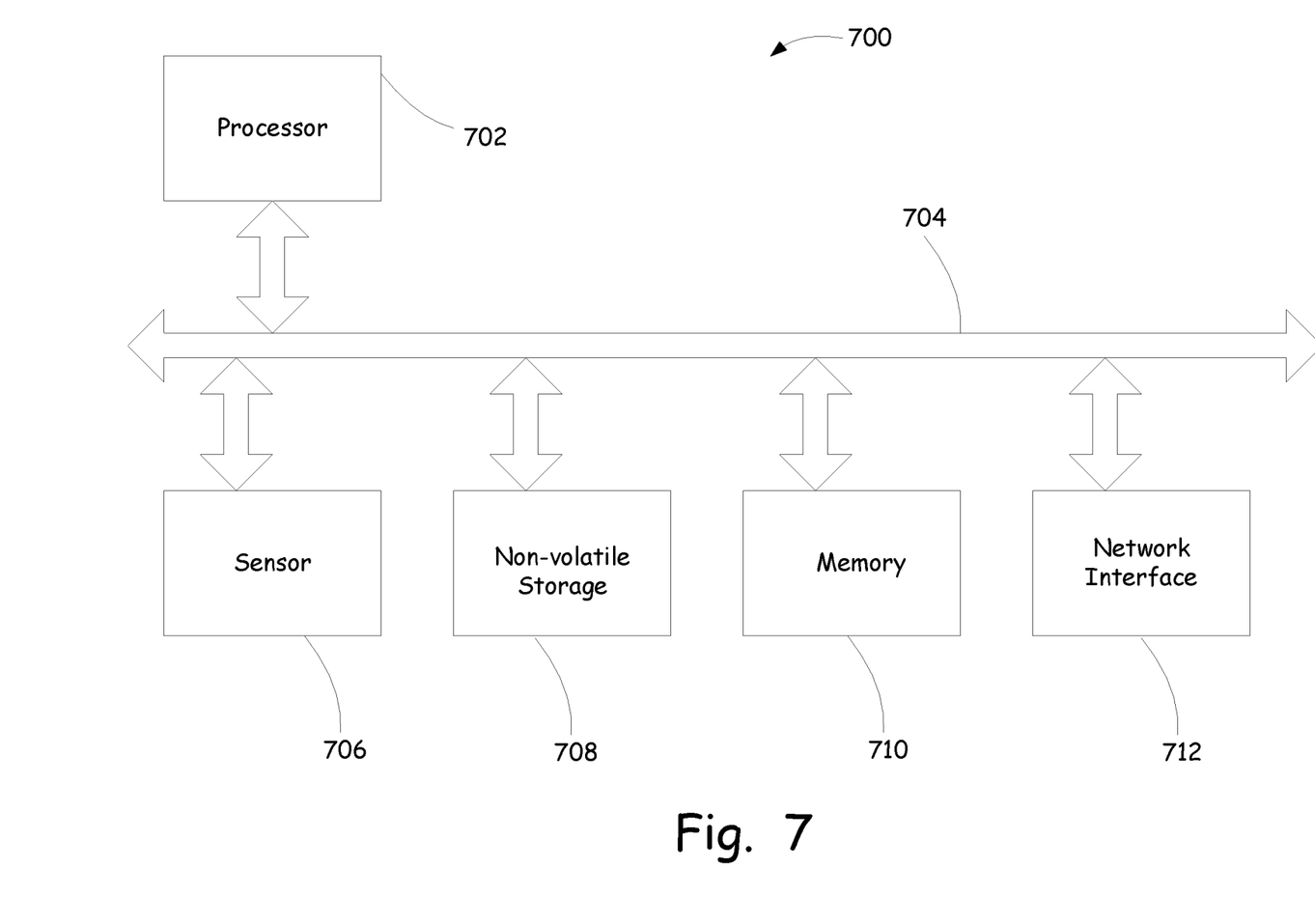
FIG. 7 illustrates an example Internet of Things (IoT) device in accordance with various example embodiments.

FIG. 7 shows a high-level block diagram of an example IoT device 700. In this example embodiment, a processor 702 may be coupled to other components of IoT device 700 by a bus 704. A sensor 606, such as, but not limited to a temperature sensor, may be coupled to bus 604. A non-volatile storage 708, such as but not limited to a hard disk drive or a flash memory, is coupled to bus 704. A memory 710, such as but not limited to a dynamic random access memory (DRAM), may be coupled to bus 704. Memory 710 may be configured to store therein instructions that may be executed by processor 702, and may be further configured to store data that does not represent instructions to be executed by processor 702. A network interface 712, such as but not limited to an Ethernet interface, may be coupled to bus 704. Network interface 712 provides a communications connection for IoT device 700 to a communications network such as, but not limited to, a local area network, or via routers, to the Internet. In one or more embodiments, IoT device 106, 206, 306 or 406 may be similar to IoT device 700. In operation, such IoT devices similar to IoT device 700, may execute instructions stored in their respective memories 710 by their respective processors 702 to implement functions such as, but not limited to, generating a first packet of data or information in a publisher-specific format or generating a second packet of data or information based, at least in part, on the content of the first packet of data or information in a processor-independent format.

Figure 8:
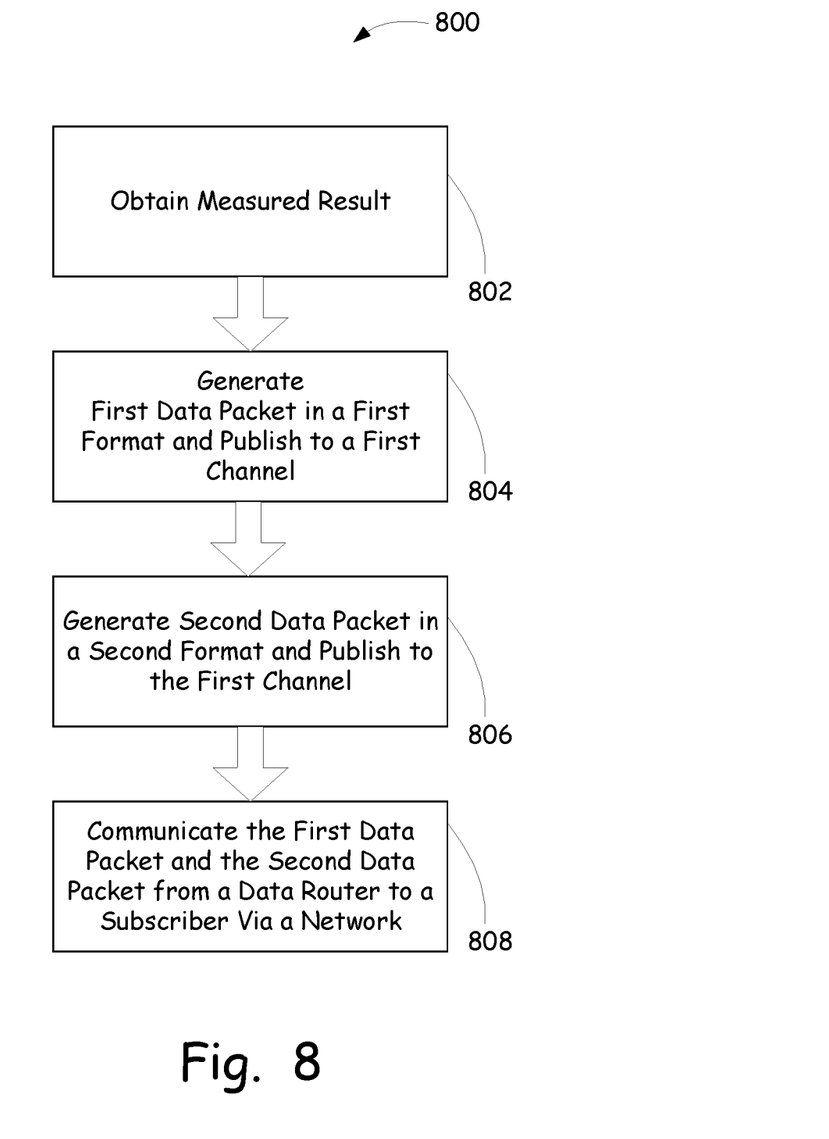
FIG. 8 illustrates an example method of producing and communicating a publisher-specific and a publisher-independent set of data packets and providing them to a subscriber via a data router through a logical channel.

FIG. 8 illustrates a flow diagram of an example method 800 for publisher-independent auxiliary communications in data router-mediated publisher/subscriber transmissions. With reference to method 800, in Block 802, a measured result is obtained. The measured result may be obtained via the operation of a device such as, but not limited to, an analyzer, an automation system, or an IoT device. For example, a blood, immunoassay, or clinical chemistry analyzer, after performing one or more testing and/or analysis operations, may obtain the result of those testing and/or analysis operations. Similarly an IoT device may obtain through the operation of its sensors and associated hardware and/or software, readings on temperature, humidity, vibration, weight, barometric pressure, hardware malfunctions, or water ionization. Method 800 further includes, in Block 804, generating a first packet in a first format and publishing the first packet in the first format to a first channel. The first packet in the first format may be the data or information obtained or generated by a publisher (e.g., an analyzer, automation system, IoT device, and the like), where the format of that data or information may be specific to the publisher. In some example embodiments, publishing to a channel by a publisher means that the publisher labels, tags, or otherwise identifies, the data or information in the publisher-specific format such that a subscriber may subsequently request information by referring to a channel rather than to one or more particular devices that publish the data or information. These labels, tags, or other identifications may be used by the data router as an index, or pointer, to store the data or information published to the channel so that the data or information can be properly retrieved from memory or storage. In this way, when a subscriber makes a request to the data router for a channel, the data router can locate the data or information that was labelled, tagged, or otherwise identified from a memory or a storage of the data router, and transmit that data or information to the requesting subscriber. Method 800 further includes, in Block 806, generating a second data packet including at least a portion of the contents of the first data packet, in a second format and publishing the second packet in the second format to the first channel. Generating the second packet in the second format may be done by the publisher of the original data or information, or may be done by the data router in those circumstances where a publisher does not generate the second packet in the second format. In some example embodiments, generation of the second packet in the second format (e.g., the format shown in Table 1 above) is accomplished by executing a program on a computer system that is included in either the publisher or the data router. Method 800 further includes communicating the first data packet and the second data packet from a data router to a subscriber via a communications network.

In some alternative embodiments in accordance with this disclosure, a data router and a process manager may be implemented on the same computer system.

In some alternative embodiments in accordance with this disclosure, a first communications network between a publisher and a data router is a different communications network than the one between the data router and a subscriber.

In some alternative embodiments in accordance with this disclosure, a data router and a process manager may be implemented on the same or different computer systems and are located remotely from the publishers.

In various example embodiments, a "data packet" is not limited to any particular size, and may include some or all of the data or information that a publisher or a data router intends to send as part of any message.

Numerous embodiments are described in this disclosure, and are presented for illustrative purposes only. The described embodiments are not, and are not intended to be, limiting in any sense.

The present disclosure is neither a literal description of all embodiments nor a listing of features that must be present in all embodiments.

When an ordinal number (such as "first," "second," "third," and so on) is used as an adjective before a term, that ordinal number is used (unless expressly specified otherwise) merely to indicate a particular feature, such as to distinguish that particular feature from another feature that is described by the same term or by a similar term. For example, a "first widget" may be so named merely to distinguish it from, e.g., a "second widget." Thus, the mere usage of the ordinal numbers "first" and "second" before the term "widget" does not indicate any other relationship between the two widgets, and likewise does not indicate any other characteristics of either or both widgets. For example, the mere usage of the ordinal numbers "first" and "second" before the term "widget" (1) does not indicate that either widget comes before or after any other in order or location; (2) does not indicate that either widget occurs or acts before or after any other in time; and (3) does not indicate that either widget ranks above or below any other, as in importance or quality. In addition, the mere usage of ordinal numbers does not define a numerical limit to the features identified with the ordinal numbers. For example, the mere usage of the ordinal numbers "first" and "second" before the term "widget" does not indicate that there must be no more than two widgets.

Devices that are in communication with each other need not be in continuous communication with each other, unless expressly specified otherwise. On the contrary, such devices need only transmit to each other as necessary or desirable, and may actually refrain from exchanging data most of the time. For example, a machine in communication with another machine via the Internet may not transmit data to the other machine for weeks at a time. In addition, devices that are in communication with each other may communicate directly or indirectly through one or more intermediaries.

A description of an embodiment with several components or features does not imply that all or even any of such components and/or features are required. On the contrary, a variety of optional components are described to illustrate the wide variety of possible embodiments in accordance with this disclosure. Unless otherwise specified explicitly, no component and/or feature is essential or required.

Further, although process steps, algorithms or the like may be described in a sequential order, such processes may be configured to work in different orders. In other words, any sequence or order of steps that may be explicitly described does not necessarily indicate a requirement that the steps be performed in that order. The steps of processes described herein may be performed in any order practical. Further, some steps may be performed simultaneously despite being described or implied as occurring non-simultaneously (e.g., because one step is described after the other step). Moreover, the illustration of a process by its depiction in a drawing does not imply that the illustrated process is exclusive of other variations and modifications thereto, does not imply that the illustrated process or any of its steps are necessary to implement various embodiments in accordance with this disclosure, and does not imply that the illustrated process is preferred.

An enumerated list of items (which may or may not be numbered) does not imply that any or all of the items are mutually exclusive, unless expressly specified otherwise. Likewise, an enumerated list of items (which may or may not be numbered) does not imply that any or all of the items are comprehensive of any category, unless expressly specified otherwise. For example, the enumerated list "a computer, a laptop, a PDA," does not imply that any or all of the three items of that list are mutually exclusive and does not imply that any or all of the three items of that list are comprehensive of any category.

A "processor" means any one or more microprocessors, Central Processing Unit (CPU) devices, computing devices, microcontrollers, digital signal processors, or like devices. Example processors are the INTEL PENTIUM or AMD ATHLON processors.

It will be readily apparent that the various methods and algorithms described herein may be implemented by a control system and/or the instructions of the software may be designed to carry out the processes in accordance with this disclosure.

As used herein a "network" generally refers to an information or computing network that provides an environment wherein one or more computing devices may communicate with one another. Such devices may communicate directly or indirectly, via a wired or wireless medium such as the Internet, LAN, WAN or Ethernet (or IEEE 802.3), Token Ring, Token Bus, or via any appropriate communications means or combination of communications means. Example protocols include but are not limited to: Bluetooth™, Time Division Multiple Access (TDMA), Code Division Multiple Access (CDMA), Global System for Mobile communications (GSM), Enhanced Data rates for GSM Evolution (EDGE), General Packet Radio Service (GPRS), Wideband CDMA (WCDMA), Advanced Mobile Phone System (AMPS), Digital AMPS (D-AMPS), IEEE 802.11 (WI-FI), IEEE 802.3, SAP, the best of breed (BOB), system to system (S2S), or the like. Note that if video signals or large files are being sent over the network, a broadband network may be used to alleviate delays associated with the transfer of such large files, however, such is not strictly required. Each of the devices is adapted to communicate on such a communication means. Any number and type of machines may be in communication via the network. Where the network is the Internet, communications over the Internet may be through a website maintained by a computer on a remote server or over an online data network including commercial online service providers, bulletin board systems, and the like. In yet other embodiments, the devices may communicate with one another over RF, cable TV, satellite links, and the like. Where appropriate encryption or other security measures such as logins and passwords may be provided to protect proprietary or confidential information.

It will be readily apparent that the various methods and algorithms described herein may be implemented by, e.g., appropriately programmed general purpose computers and computing devices. Typically a processor (e.g., one or more microprocessors) will receive instructions from a memory or like device, and execute those instructions, thereby performing one or more processes defined by those instructions. Further, programs that implement such methods and algorithms may be stored and transmitted using a variety of media (e.g., computer readable media) in a number of manners. In some embodiments, hard-wired circuitry or custom hardware may be used in place of, or in combination with, software instructions for implementation of the processes of various embodiments. Thus, embodiments are not limited to any specific combination of hardware and software. Accordingly, a description of a process likewise describes at least one apparatus for performing the process, and likewise describes at least one computer-readable medium and/or memory for performing the process. The apparatus that performs the process can include components and devices (e.g., a processor, input and output devices) appropriate to perform the process. A computer-readable medium can store program elements appropriate to perform the method.

The foregoing description discloses only example embodiments. Modifications of the above-disclosed apparatus and methods which fall within the scope of this disclosure will be readily apparent to those of ordinary skill in the art. For example, although the examples discussed above are illustrated for health information systems, other embodiments in accordance with this disclosure can be implemented for other markets.

What is claimed is:

1. A method, comprising:
   obtaining, by a first device, a first measured result;
   generating, by the first device, a first data packet in a first format, the first data packet based, at least in part, on the first measured result, and the first format associated with the first device;
   generating, by the first device, a second data packet in a second format, the second data packet based, at least in part, on a portion of the first data packet, and the second format being independent of the first device; and
   transmitting the first data packet in the first format and the second data packet in the second format via a first communications network;
   wherein the second data packet in the second format contains actionable information derived from the first data packet in the first format, and wherein the first device comprises an analyzer, an automation system, or an Internet of Things device.

2. The method of claim 1, further comprising:
   obtaining, by an automation system, data related to a status of one or more automation system functions to produce a first automation system report.

3. The method of claim 1, further comprising:
   obtaining, by an Internet of Things device, data related to a sensor of the Internet of Things device to produce a first IoT report.

4. The method of claim 1, wherein obtaining the first measured result comprises:
   obtaining temperature, humidity, barometric pressure, vibration, inventory scale, hardware malfunction, clinical result, or water ionization reading.

5. The method of claim 1, further comprising:
   receiving, by a data router, the first data packet in the first format and the second data packet in the second format.

6. The method of claim 5, further comprising:
   transmitting, by the data router, the first data packet in the first format associated with the first device and the second data packet in the second format independent of the first device, to a subscriber.

7. The method of claim 6, further comprising:
   initiating, by the subscriber, a control action based on the second data packet in the second format prior to processing, by the subscriber, the first data packet in the first format.

8. A method, comprising:
   obtaining, by a device, a first measured result;
   generating, by the device, a first data packet in a first format, the first data packet based, at least in part, on the first measured result, and the first format associated with the device;
   transmitting, by the device, the first data packet in the first format to a data router via a first communications network;
   generating, by the data router, a second data packet in a second format, the second data packet based, at least in part, on a portion of the first data packet, and the second format being independent of the device; and
   transmitting, by the data router, the first data packet in the first format and the second data packet in the second format to a subscriber via a second communications network;
   wherein the second data packet in the second format contains actionable information derived from the first data packet in the first format, and wherein the device comprises an analyzer, an automation system, or an Internet of Things device.

9. The method of claim 8, wherein the first communications network and the second communications network are different.

10. The method of claim 8, further comprising:
    obtaining, by an automation system, data related to a status of one or more automation system functions to produce a first automation system report.

11. The method of claim 8, further comprising:
    obtaining, by an Internet of Things device, data related to a sensor of the Internet of Things device to produce a first IoT report.

12. The method of claim 8, wherein obtaining the first measured result comprises:
    obtaining temperature, humidity, barometric pressure, vibration, inventory scale, hardware malfunction, clinical result, or water ionization reading.

13. The method of claim 8, further comprising:
    transmitting, by the data router, the first data packet in the first format associated with the device and the second data packet in the second format independent of the device, to a subscriber.

14. The method of claim 13, further comprising:
    initiating, by the subscriber, a control action based on the second data packet in the second format prior to processing, by the subscriber, the first data packet in the first format.

15. A health information system, comprising:
    a first device configured to obtain a measured parameter, and further configured to generate a first data packet in a first format, the first data packet based, at least in part, on the measured parameter, and the first format associated with the first device;
    a subscriber;
    a data router coupled to the first device via a first network and coupled to the subscriber via a second network, the data router comprising:
       a processor;
       a memory, coupled to the processor, the memory having stored therein a plurality of instructions that, when executed by the processor, causes the data router to:
          receive the first data packet in the first format via the first network,
          generate a second data packet in a second format, the second data packet based, at least in part, on a portion of the first data packet, and the second format being independent of the first device, and
          transmit the first data packet and the second data packet to the subscriber via the second network;
       wherein the second data packet in the second format contains actionable information derived from the first data packet in the first format.

16. The health information system of claim 15, wherein the first device comprises an analyzer.

17. The health information system of claim 15, wherein the first device comprises an automation system.

18. The health information system of claim 15, wherein the first device comprises an Internet of Things device.

19. The health information system of claim 15, wherein the first network and the second network are different.

20. An apparatus, comprising:
    a processor; and a memory coupled to the processor, the memory having instructions stored therein that, when executed by the processor, cause the apparatus to:
obtain a first measured result,
generate a first data packet in a first format, the first data packet based, at least in part, on the first measured result, and the first format associated with the apparatus,
generate a second data packet in a second format, the second data packet based, at least in part, on a portion of the first data packet, and the second format being independent of the apparatus, and
transmit the first data packet and the second data packet via a communications network;
wherein the second data packet in the second format contains actionable information derived from the first data packet in the first format.

* * * * *